United States Patent
Brady et al.

(12) 
(10) Patent No.: US 6,410,337 B1
(45) Date of Patent: *Jun. 25, 2002

(54) METHOD OF PLATLET FUNCTION ANALYSIS USING PLATELET COUNT

(75) Inventors: Terry Brady, Gladstone; Michael F. Corsello, West Milford, both of NJ (US)

(73) Assignee: Helena Laboratories Corporation, Beaumont, TX (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/933,181

(22) Filed: Sep. 18, 1997

(51) Int. Cl.$^7$ ............................................. G01N 33/86
(52) U.S. Cl. .......................... 436/69; 436/63; 422/61; 422/73; 73/64.41
(58) Field of Search .................... 436/63, 69, 149, 436/150; 422/68.1, 61, 73, 82.01, 82.02; 73/64.41, 64.42

(56) References Cited

U.S. PATENT DOCUMENTS

| | | | | |
|---|---|---|---|---|
| 4,788,139 A | * | 11/1988 | Ryan | 435/13 |
| 5,091,304 A | * | 2/1992 | La Duca et al. | 435/13 |
| 5,266,462 A | * | 11/1993 | Henker et al. | 435/13 |
| 5,314,826 A | * | 5/1994 | Baugh | 436/69 |
| 5,523,238 A | * | 6/1996 | Varon et al. | 436/69 |
| 5,563,041 A | * | 10/1996 | Reers | 435/13 |
| 5,602,037 A | * | 2/1997 | Ostgaard et al. | 436/69 |
| 5,925,319 A | * | 7/1999 | Baugh et al. | 422/73 |
| 5,951,951 A | * | 9/1999 | Lane et al. | 422/73 |

OTHER PUBLICATIONS

Saniabachi et al. *Thrombosis Research*, vol. 30, No. 6, pp. 625–632, 1983.*

Sweeney et al. *American Journal of Clinical Pathology*, vol. 92, No. 6, pp. 794–797, Jan. 1990.*

* cited by examiner

Primary Examiner—Maureen M. Wallenhorst
(74) Attorney, Agent, or Firm—Jerold I. Schneider

(57) ABSTRACT

A method for determining platelet activation by utilizing numeric counts of platelets before a sample of platelets has been activated and after the activatable platelets are activated with a platelet activation agonist and using the difference between such counts as an indication of the platelet activity of the sample. There is also disclosed a method for using the electronic impedance cell counting technique for determining platelet activation wherein EDTA is used as a preservative by counting the platelets in an EDTA preserved sample using an electronic impedance cell counting technique and subtracting from that number the number of platelets remaining after the activatable platelets in a second sample have been activated with a platelet agonist in the absence of EDTA and using that difference as a measure of platelet activity.

14 Claims, No Drawings

METHOD OF PLATLET FUNCTION ANALYSIS USING PLATELET COUNT

This invention relates to determination of platelet function (aggregation, agglutination, and adhesion) using a differential cell counting technique. More specifically, the invention relates to the use of a common laboratory based instrumentation technology in a new method for determining the viability of platelets and platelet function and adhesion by obtaining a platelet count in the instrument before and after intentional platelet activation.

BACKGROUND

Platelets are biological cells in blood circulation that provide the first line of hemostatic defense. They contribute the initial physiology and biochemistry to maintain normal circulatory integrity to help prevent exsanguination or bleeding to death upon injury, especially venous or vascular injury. Life cannot be maintained without adequate platelet numbers and without some meaningful degree of platelet functionality or quality.

Platelets are irregularly-shaped, colorless bodies which are normally present in blood at the level of about 250,000 cells per $mm^3$. Their sticky surfaces, along with other endogenous substances or stored chemicals, act to form primary platelet plugs and ultimately, stable blood clots to stop or arrest bleeding. When bleeding from a wound suddenly occurs, the platelets stick to the wound site and release substances that cause them to gather (aggregate), en masse at the venous injury. This prevents excessive blood from escaping the vasculature, thus preventing irreversible morbidity and mortality. Other coagulation proteins in the blood in concert with the platelets form a fibrin clot usually within minutes.

Coagulation (or blood clotting) and platelet activation, adhesion, and aggregation occur when blood is exposed to non-biological material including any material that is dissimilar to venous endothelium and more importantly, biological materials such as an injured blood vessel. Often, during the routine practice of medicine, blood may be exposed to a hostile, platelet-activating environment such as contact with an extracorporeal blood circuit or the results of invasive procedures that injure the vascular lining or exposure of the blood to air. The platelets normally respond to this condition and begin to activate. After activating, the platelets react with specific coagulation plasma proteins and fibrinogen to begin forming fibrin, tiny thread-like visible strands of protein. These fibrin threads link to form a web-like mesh that traps red cells, white cells, and platelets, leading to the formation of a stable or insoluble clot. On the skin surface, the blood clot is ultimately transformed from an initial plug to arrest bleeding to a healing process in which the blood clot becomes a crusty protective layer of cells (scab).

Platelets that have the ability to activate are commonly called "sticky" and "functional" platelets. The extent to which these platelets activate or perform qualitatively is variously called platelet activity, platelet function, platelet aggregation, or platelet adhesion. Once the platelet has performed its qualitative aggregation function fully, the endogenous biochemistry has been consumed and cannot be recharged or revitalized. The sticky or adhesive quality of the platelet may still provide hemostatic support in microcirculatory physiology, but the biochemical aggregating quality of the platelet is a one time event or occurrence.

Platelet quality is also affected both positively and negatively by contemporary over-the-counter drugs and by hospital-based pharmacology compounds. Platelet function characteristics may also be manipulated by certain agents to better control specific medical procedures and surgeries. Some compounds are used to slightly alter platelet function by causing intentional temporary dysfunctionality, as in the case of aspirin therapy, for heart disease patients who are more prone to thrombosis or clot. Aspirin is used to minimize platelet adhesion and cause qualitative platelet defects that are nevertheless beneficial to patient well-being.

Clinically, platelet assessment is a very useful parameter and provides relevant information regarding a patient's hemostatic or bleeding status and thrombotic state.

Even though platelets are uniquely associated with, and are a contributor to thrombosis, a leading cause of morbidity and mortality, the technology to measure and predict platelet physiology is lacking and sorely needed. There are a very limited number of ways (mostly unsatisfactory) to measure platelet function both qualitatively and quantitatively. Notable accepted laboratory methods include:

Bleeding Time (a qualitative, not quantitative, measure): In this procedure, a small invasive incision is made in the forearm after placing a blood pressure cuff on the same arm and inflating it to 40 mm Hg. As blood exudes from the wound it is blotted with filter paper, and the time at which bleeding stops is recorded. The normal bleeding time is usually less than 9–10 minutes. The Bleeding Time test is commonly performed as part of the pre-operative patient screen. The test is laborious and expensive and the time and personnel requirements prevent this test from being performed routinely or even effectively in the operating room.

Platelet Aggregometry (quantitative platelet measurement considered to be the reference method): This assay measures the level or percent of functionality platelet activity in patient plasma and is reported in percent platelet aggregation. The assay is performed by briefly pre-incubating normal human platelet-rich plasma and adding a known platelet aggregation agent (e.g. ristocetin, collagen, etc.) in a traditional platelet aggregometer. Aggregometry works on a simple photometric principle and does not use a numeric counting technique. The amount of light that passes through a platelet-rich plasma sample in aggregometry is low and is electronically calibrated to zero. This is compared to maximum or 100 percent light transmission through platelet-poor plasma (sometimes called platelet-free plasma), due to the lack of light absorption by the platelets.

By adding a platelet aggregating agent to the platelet-rich plasma, the platelets are caused to clump or aggregate and separate from the liquid phase. Light transmission thus increases as the platelet-rich plasma sample becomes more translucent as compared to the 100 percent light transmission of control platelet-poor plasma. The principle of this test is that the interaction between the aggregating agent and the platelets causes the activation of the platelets, subsequently leading to platelet activation, adhesion, and aggregation, or simple "clumping". The functional platelets are thus trapped in the platelet aggregate or "clump". This clumping allows an increasing proportionate level of light to now pass through the platelet-rich plasma patient sample. The difference in the two samples (pre-clump and post-clump) are compared as a percentage. The level of functional platelets or percent aggregation is determined by comparison of the percent difference between light transmission of platelet-poor plasma and that of platelet-rich plasma following the addition of the known aggregating agent.

Normal platelets and disease or damaged platelets are accurately characterized by using a variety or combination of chemicals or known aggregating agents. When these agents are used in known concentrations, an accurate depiction of disease and seriousness of platelet damage or dysfunction can be identified when using the aggregometer. There are numerous platelet adhesion and aggregating agents with differing platelet response. Concentrations of aggregating agents has become specific to diagnostic, disease, and dysfunctionality.

Aggregating agents or platelet activation agonists referred to above may include adenosine 5' di-phosphate, adenosine tri-phosphate, serotonin, thromboxane, collagen, epinephrine, thrombin, ristocetin, arachidonic acid, and the like. They may be used as aggregating agents and agonists in the present invention as well.

The adhesion or "sticky" quality of platelets can also be measured using glass beads as the reagent in the present invention because platelets have an affinity to glass and platelet adhesion has a linear response to glass and glass-like materials, (e.g. fiberglass). In general, this test involves running platelets over a glass bead column, collecting the run-through and determining the number of platelets that adhere to the glass bead surfaces as a percentage of the total platelets allowed to flow over the beads. This technique is not commercially available and as such has not reached any satisfactory level of acceptance by the art. This characteristic is nevertheless uniquely important following coronary bypass surgery as micro vascular bleeding is common and the adhesion quality of platelets is vital when arresting tiny vessel or capillary and capillary-like bleeding.

These platelet aggregometry and adhesion procedures are arduous, time-consuming, expensive, and require tedious blood specimen collection, handling, and processing procedures. Consequently, these techniques are error-prone. Another complicating aspect is the unstable nature of platelet adhesion and function (or aggregation). The aggregation test is largely performed in only the more advanced or specialty hemostasis laboratory environments and as such, platelet function testing is rarely performed even though platelet viability is a major and routine indication for blood transfusion, including emergency transfusions Consequently, most blood and blood platelet transfusions are given without a platelet functionality indication or laboratory support. Platelet aggregometry is typically reserved for the diagnosis of a rare congenital bleeding disorder and are not often used to better transfuse blood and blood platelets regardless of the indications and recommendations for platelet transfusion. Further, platelet aggregometry is not typically offered as a STAT test and is most often a scheduled test by appointment with a laboratory.

Electronic Blood Cell Counting

Prior to modern electronics, hematological blood cell counting (commonly called the CBC or complete blood count) was done manually and with relative accuracy regarding red and white blood cells. The reference method for red cells was the spun haematocrit; and for white cells, it was a staining technique that was then read on a phase microscope. Platelet counts were less satisfactory using manual methods or microscopes because of their small size and instability (activating or clumping). Electronic cell counting enjoyed early success regarding red cells and white cells, but platelet counts were more problematic, for the same reasons as mentioned above, regarding manual counts. Contemporary hematology analyzers or cell counters are sophisticated and highly reliable high capacity multichannel devices. They typically employ the technique of measuring changes in electrical impedance as the cells and platelets flow through a small aperture with computer analysis of the electrical signals generated. In effect, the cell counter identifies a cell type (white cell, red cell, and platelet) by size, shape, and mass. The red cell has a diameter of approximately 7.5 microns, and platelets are elongated measuring approximately 3 microns in length and 1 micron in thickness White cells are larger than red cells and will range in sizes typically above 7 microns to over 20 microns and will vary in shape from multi-lobed to spherical, and non-uniform to almost round. Commonly called the Coulter Counter (also a branded product) or Coulter Principal, the electronic cell counter technologies are manufactured by numerous companies today including Coulter Electronics, Miami, Abbott Laboratories, Chicago, ABX, France, and others, the details of construction and use of which are incorporated herein by reference. Routine CBC analysis is likely the most widely-performed multi-parameter biologic test in the world.

The CBC instruments and methodology described above are herein referred to as electrical impedance cell counters (EICC) or simply CBC instruments, by which terms are meant the art-known passage of cellular blood components, in a dilute medium through an aperture and the numeric counting of cells by reason of the changes caused in the electrical conductivity of the medium as the cells pass the measuring electrodes. While electrical impedance cell counters are very effective to count platelets, no information is obtained on platelet function, that is, the ability of the platelets to exert their required function in body physiology. Remarkably, platelet functionality and "stickiness" characteristics have always been considered a problem regarding cell counting, and the preservatives used to collect whole blood for blood cell counting are designed specifically to disable the functionality and adhesion characteristics of platelets. This blood collection preservative is EDTA (ethylene diamine tetracetic acid) and is used worldwide in standard blood collection test tubes (often referred to as simply a purple-top blood collection tube). Blood and blood platelets preserved in EDTA will not respond to aggregating or adhesion agents or medium.

As noted above, one is able to count platelets on EDTA-preserved blood using the CBC counter. One cannot determine platelet function, however, using the counting technique in the CBC counter in the presence of EDTA because the EDTA prevents the platelets from aggregating even in the presence of activating agents or agonists. Those skilled in the art are well aware that EDTA prevents aggregation of the platelets in the presence of agonists. Therefore, the art has thought that while the CBC instrument is eminently useful in counting cells, it is not useful in determining platelet function.

In the CBC determination, the starting material is diluted whole blood, generally preserved with EDTA. Those skilled in the art have recognized that EDTA alters the platelet function in such a way as to preclude measurement via activation by platelet agonists. Therefore, it is not possible to induce activation of platelets to cause clumping in the presence of EDTA. The art has not heretofore found a way to determine the activity of platelets in whole blood and then to evaluate the number of platelets which can be activated largely because the CBC instrument process has been restricted to the use of EDTA.

SUMMARY OF THE INVENTION

Through the present invention, a method has now been discovered which enables the counting technique involved in the CBC instrument to be used to determine platelet function. In fact, the invention is versatile enough to permit the platelet function to be performed on a CBC instrument without changes in hardware and by using the following simple math equation as will be described more fully below. This is done through the use of an additional sample tube containing materials which activate the platelets in the diluted whole blood sample. The activated platelet mixture is used as another sample whose platelets are also to be counted on the CBC instrument. From this procedure, the number of platelets activated vs. the number of platelets originally present (in the first tube analyzed according to standard CBC counting protocol) are determined to give a measure of platelet activation and platelet function. Secondarily, platelet adhesion can be measured using the same technique and by having a glass bead agonist or another glass-like particle or other material platelet attracting substance that causes the platelet to "stick" or adhere to the material in a controlled, predictable manner. The platelets that were counted are those which do not stick to or aggregate to any other platelets and are therefore seen and counted by the cell counter. Counted platelets were therefore non-sticky and therefore non-functional.

The present invention takes advantage of the difference in the numeric count of platelets obtained from an initial inactivated sample of human or animal platelets from the count of platelets left in a sample in which activating reagents for activating the function of the platelets have been added to cause the platelets to clump or aggregate or adhere. In a cell counter, two platelets that have aggregated, joined or clumped together will generally measure over 6 microns and may be mischaracterized as either a red cell or a white cell, but never a platelet. Since the platelet is the smallest cell that can be counted in a CBC instrument, two or more platelets joined or clumped together will always be measured as something other than a platelet. From a platelet functionality perspective, the fact that two or more platelets aggregated or clumped together when using this invention becomes a specific and direct measure of platelet viability, aggregation, and/or adhesion. Further, the cell counter may be programmed to look for only unaggregated platelets and to ignore all other particles or cells larger than platelets. In this manner, the counting procedure disregards the clumped aggregates and will only report, assuming it is properly so programmed, the unclumped platelets. The clumped platelets thus represent the active platelets and the percent of functional platelets is easily determined from the counting procedure by dividing the difference between the baseline and aggregated count by the baseline count.

When using a CBC hematology instrument, the invention is usually carried out in the following manner:

A first tube and a second tube of patient's properly diluted whole blood or platelet-containing plasma are provided. The platelet counts according to the invention are obtained on the samples in the tubes. It should be apparent to those skilled in the art that to the extent that the two tubes differ in the number of platelets present in each sample, the test results will be diminished in reliability. Ideally, an equal number should be present in each. The first tube is placed into the usual CBC hematology instrument for counting of platelets (in addition to the other blood cell components, if desired). The first tube will also no doubt contain EDTA as the preservative if a standard CBC protocol is followed. Therefore, the first step in one embodiment of the invention is to obtain a platelet count baseline on EDTA-preserved, diluted whole blood (or platelet-containing plasma) using the CBC hematology instrument just as it has been and is currently conducted in accordance with known techniques.

It should be noted that the invention does not require that the baseline be taken on EDTA-preserved blood. The baseline platelet count may be obtained on any viable sample in which unactivated platelets can be counted as long as there is a reasonable certainty that an accurate count can be obtained irrespective of the preservative employed. EDTA-preserved blood is described here simply because EDTA is the preservative of choice in CBC instrument counting and it is in that environment that the art has been prevented from counting activated platelets.

In addition, while the advantages and results of the invention are most readily obtainable and observable using the CBC counting methodology, it should be emphasized that platelet function according to the invention may be obtained using any platelet numeric counting methodology as long as the platelets count in the sample after activation is compared to any appropriate baseline numeric count within a suitable timeframe irrespective of the method of counting.

In this presently discussed embodiment of the invention, a platelet count is next obtained on the sample in the second tube. This tube contains patient whole blood sample, diluted as it would be for normal platelet counting in a CBC instrument, but instead of containing EDTA, if it contains a platelet preservative at all, it contains one which does not interfere with platelet aggregation or function (i.e. one which is substantially inert to platelet aggregation and has little or no effect on platelet function). Sodium citrate is a blood preservative which does not interfere with induction or initiation of platelet activation by platelet agonists and is a preferred preservative if one is used in practicing this invention. In addition, the tube contains a platelet activity inducing agent (agonist). As agonists, there may be used any of the ones previously discussed above or any others known in the art for activating platelets. Preferred in this embodiment is ADP.

In addition, it is often desired and in some cases preferred, to provide within the second tube, glass beads or some other surfaces to provide a vehicle which acts as an adhesion surface to which the activated platelets will be attracted and thus removed from the suspension. It is not required that such a surface be provided since, in many cases, the surface of the glass tube will provide that function.

Once the whole blood or diluted whole blood is present in the second tube in the presence of the inert preservative and the agonist, the contents of the tube are gently mixed end-to-end usually for about 30 seconds to several minutes depending on the constituents to allow the agonist to induce the activity of the platelets and initiate the clumping of the active platelets. Naturally, it is preferred that the amount of agonist and the length of time employed in activation be sufficient to activate the maximum number of platelets in order to achieve accurate measurements. The temperature is normally from room temperature to normal body temperature as required by the testing environment. It should be noted, of course, in view of what has been said previously about the function of EDTA and its deleterious effect on the activity of the platelets in the presence of an agonist, that the second tube should not contain any detrimental amounts of EDTA or any similar materials having a depressant effect on platelet activation.

The normal CBC instrument platelet counting procedures performed on each of the above samples results in a delta between the platelet baseline count of the first tube and the count obtained on the second tube containing activated clumped platelets. The delta is used to determine a number characterizing the number of functional platelets in the sample. Activated platelets are not available for the platelet count and, therefore, a simple delta between the counts can give the level of platelet functionality in a sample. For example, if the baseline count is 100,000/mm$^3$ and the unactivated platelet count in the activated tube is 40,000/mm$^3$, that means that 60,000 platelets were activated (and clumped or aggregated together) and not seen and, therefore, not counted as platelets by the cell counter yielding a percentage of platelet function of 60% (i.e. [(100,000–40,000) divided by 100,000]×100). Another more typical and healthier platelet example is a EDTA platelet count of 276,588/mm$^3$ and an unactivated platelet count of 32,000/mm$^3$ measured by cell counter after activation and platelet aggregation. [(276,588–32,000) divided by 276,588]×100= 88% aggregation.

The present invention both in the form of its product and process modalities is extremely versatile in that it can be employed to diagnose various platelet dysfunctions. For example, once a platelet activity is determined on a sample, various reagents can be added to additional tubes in order to assess the effect of different agents on the activation of platelets. Accordingly, it is possible to evaluate the efficacy of antifibrinolytic or platelet protectorate such as aprotinin and transexamic acid as well as DDAVP, aminocaproic acid, and aspirin to determine the levels, if any, of inhibition, suppression or enhancement these products have on the ability of the platelets to function when stimulated. In a similar manner, IIb–IIIa anti-platelet compounds can be measured therapeutically when using this invention. Likewise, patients who have congenital or acquired platelet disorders can be diagnosed and characterized. The invention can thus be used to determine accurate dosages of the in vivo use of some of the above-mentioned compounds. The invention also contemplates having additional tubes which contain one or more of such materials to be supplied for use on the hematology cell counting instruments. As an example, to diagnose storage pool disease (a well-articulated platelet disorder), a combination of aggregating agents like collagen, epinephrine, ADP, and ristocetin in specific concentrations would provide differing aggregation responses such that a differential diagnosis may be offered. Similar, yet more dramatic, circumstances would be the differential diagnosis of bleeding post coronary bypass surgery, which could result in precise transfusion information such that the correct blood component could be prepared and infused.

A novel article of manufacture, under this invention, is a tube which contains an appropriate amount of an agonist for activating platelets and optionally a preservative which does not interfere with platelet function. A preferred agonist is ADP and a preferred preservative is sodium citrate. The agonist is normally present in amounts which are known to be effective in activating the amount of platelets expected to be encountered in the second tube. A useful kit, therefore, comprises a first tube which contains EDTA or some other preservative for blood on which the first counting on the CBC instrument is performed accompanied by a second tube which has the ingredients aforementioned.

Most conveniently, the second tube is supplied to the user of the CBC instrument on which the process of the invention is to be performed already containing either or both of the so-called inert preservative and the agonist.

By varying the agonists present in the sample tube, one may obtain a kit having a plurality of agonists each of which is contained in a separate tube to be used as the second sample in the counting technique. This would enable one to evaluate the activating ability of the agonist on the particular platelets presented for sampling and counting. The tubes may include, instead of agonists, any material desired to be evaluated for their ability to suppress or enhance the ability of the platelets to function when stimulated.

The products of the invention can be included in a kit which comprises one or more tubes containing an agonist as aforementioned and optionally a preservative which does not interfere with the platelet function or one which may interfere with platelet function to a known degree and therefore can be factored out of any results obtained on that tube. The added compounds can be supplied in lyophilized form or may be in the form of physiologic saline solutions or suspensions thereof.

The actual amounts of materials, concentrations, dilutions, and the like are all well-known in the hemotasis and cell counting field and are easily determined and adjusted depending upon the user's particular preferences and the objectives sought. A typical CBC instrument cell counter dilutes a whole blood sample by adding 1 part thereof to 183 parts of physiologic saline. 27.5 ul of this dilution are then mixed with 3 ml of physiologic saline as the diluent resulting in a dilution of 1/20,000. This is the sample upon which the counts are obtained.

Illustrative of presently preferred reagents, concentrations, and volumes to yield suitable results in the invention are the following:

| I. | Agonists: | |
|---|---|---|
| | 1. Collagen, aqueous solution, 2mg/ml | diluted 1 part with 19 parts of saline (100 ug/ml) to make a collagen stock solution |
| | 2. ADP (2 × 10$^{-4}$ mol/L) | |
| | 3. Epinephrine (1 × 10$^{-4}$ mol/L) | dilute 1 part to 9 parts of saline to make a stock solution |
| | 4. Ristocetin (15 mg/ml) | in water |
| II. | Whole Blood Dilution (prior to testing) | |
| | 1. Tube A | whole blood diluted 1:1 with saline |
| | 2. Tube B | whole blood diluted 1:1 with saline |
| III. | Volumes for testing: | |
| | 1. Collagen: | 1 ml of blood dilution from II + 500 ul of Collagen Stock solution (100 ug/ml) |
| | 2. ADP: | 3 ml of blood dilution from II + 25 ul ADP |
| | 3. Epinephrine: | 2 ml of blood dilution from II + 20 ul epinephrine stock solution |
| | 4. Ristocetin: | 1 ml of blood dilution from II + 60 ul ristocetin solution |

By way of illustration, the diluted whole blood in Tube A is further diluted according to III leaving the agonists out, but maintaining the same liquid volumes. This constitutes the sample presented to the CBC instrument which will further dilute that sample in accordance with its normal dilution regime. Baseline platelet count is obtained on Tube A. Tube B is diluted with the volumes and the agonists as set forth in III above which is then presented to the CBC instrument for dilution and counting as described for Tube A.

The above are not to be considered as limiting amounts of reagent concentrations and volumes, but are only illustrative. These amounts may vary within wide ranges without departing from the scope of the invention. For example, multiples and fractions of the above dilutions and concentrations may be employed depending upon the particular modes of testing involved and the objectives sought in the testing. Those skilled in the art are capable of selecting such variables in consideration of optimization of the procedures.

What is claimed is:

1. A method for measuring platelet function by the counting of platelets before and after exogenous platelet activation comprising:

(a) selecting first and second samples comprising platelets in a liquid medium from a physiological source of said platelets wherein each of said samples contains approximately the same number of platelets;

said first sample containing a substance which suppresses platelet activation and said first sample being essentially devoid of any agent which produces exogenous platelet activation to cause the platelets therein to aggregate;

said second sample being essentially devoid of any agent that interferes with platelet function;

(b) counting the platelets in said first sample in the absence of an activation agonist to obtain a baseline count of the platelets;

(c) mixing an amount of at least one activation agonist with said second sample to produce exogenous platelet activation for a period of time effective to maximally activate and cause aggregation of activatable platelets in said second sample;

(d) counting the platelets in said second sample after exogenous platelet activation to obtain a second count of unactivated platelets in said second sample; and (e) utilizing the difference between the baseline count of platelets in step (b) and the second count obtained in step (d) as a measure of the activity of the platelets in the physiological source.

2. The method of claim 1 wherein the baseline count and the second count of platelets are obtained with an electrical impedance cell counter.

3. The method of claim 1 wherein the substance which suppresses platelet activation in said first sample is EDTA.

4. The method of claim 1 wherein the second sample contains a preservative which does not interfere with platelet function to any significant degree.

5. The method of claim 4 wherein the preservative in the second sample is sodium citrate.

6. The method of claim 1 wherein the at least one activation agonist is selected from the group consisting of collagen, adenosine 5' di-phosphate (ADP), adenosine tri-phosphate (ATP), serotonin, thromboxane, thrombin, arachidonic acid, epinephrine, ristocetin, glass beads, and fiberglass.

7. The method of claim 1 wherein the platelets are human platelets.

8. A kit for performing the method of claim 1, said kit including first and second test tubes for said first and second samples, respectively;

said first test tube being initially devoid of any sample and being essentially devoid of any agent which produces exogenous platelet activation to cause platelets to aggregate, but including said substance which suppresses platelet activation; and said second test tube being initially devoid of any sample and being essentially devoid of any agent that interferes with platelet function but including said at least one activation agonist which will produce exogenous platelet activation for a period of time effective to maximally activate and cause aggregation of activatable platelets.

9. The test kit of claim 8 wherein said second test tube further includes a preservative which does not interfere with platelet function to any significant degree.

10. A test kit for use in obtaining platelet counts on platelet samples as a measure of the activity of the platelets, said test kit comprising:

a first tube for receiving a first sample containing platelets;

said first tube prior to receiving any sample being essentially devoid of any agent which would produce exogenous platelet activation in the presence of platelets, to cause platelets to aggregate;

said first tube prior to receiving any sample including a substance which suppresses platelet activation when in contact with a sample which includes platelets; and a second tube for receiving a second sample containing platelets;

said second tube prior to receiving any sample being devoid of any agent that interferes with platelet function when in contact with a sample which includes platelets;

said second tube prior to receiving any sample further including a platelet activation agonist in an amount effective to maximally activate and cause aggregation of activatable platelets when in contact with a sample which includes activatable platelets.

11. The test kit of claim 10 wherein said second test tube, prior to receiving any sample, contains a preservative which will not interfere to any significant degree with the activity of said agonist when in contact with a sample which includes platelets.

12. The test kit of claim 10 wherein:

said substance in said first test tube which suppresses platelet activation when in contact with a sample which includes platelets is EDTA.

13. The test kit of claim 10 wherein:

said platelet activation agonist in said second tube is selected from the group consisting of collagen, adenosine 5' di-phosphate (ADP), adenosine tri-phosphate (ATP), serotonin, thromboxane, thrombin, arachidonic acid, epinephrine, ristocetin, ,glass beads, and glass-like materials.

14. The test kit of claim 13 wherein:

said substance in said first test tube which suppresses platelet activation when in contact with a sample which includes platelets is EDTA; and said second test tube, prior to receiving any sample, contains a preservative which will not interfere to any significant degree with the activity of said agonist when in contact with a sample which includes platelets.

* * * * *